United States Patent

Wada et al.

Patent Number: 5,154,750
Date of Patent: Oct. 13, 1992

[54] PYRIMIDIEN DERIVATIVES AND HERBICIDAL COMPOSITIONS CONTAINING THE SAME

[75] Inventors: Nobuhide Wada, Kakegawa; Ryo Yoshida, Shizuoka, both of Japan

[73] Assignees: Kumiai Chemical Industry Co. Ltd.; Ihara Chemical Industry Co., Ltd., both of Tokyo, Japan

[21] Appl. No.: 745,879

[22] Filed: Aug. 16, 1991

[30] Foreign Application Priority Data

Aug. 22, 1990 [JP] Japan .................................. 2-220616

[51] Int. Cl.⁵ .................... C07D 403/12; A01N 43/54
[52] U.S. Cl. .......................................... 71/92; 544/296
[58] Field of Search .............................. 71/92; 544/296

[56] References Cited

U.S. PATENT DOCUMENTS 4,906,285  3/1990  Wada et al. .............................. 71/92

FOREIGN PATENT DOCUMENTS 223406   5/1987  European Pat. Off. .
287072  10/1988  European Pat. Off. .
287079  10/1988  European Pat. Off. .
321846   6/1989  European Pat. Off. .
346789  12/1989  European Pat. Off. .

*Primary Examiner*—John M. Ford
*Attorney, Agent, or Firm*—Oblon, Spivak, McClelland, Maier & Neustadt

[57] ABSTRACT

A pyrimidine derivative having the formula,

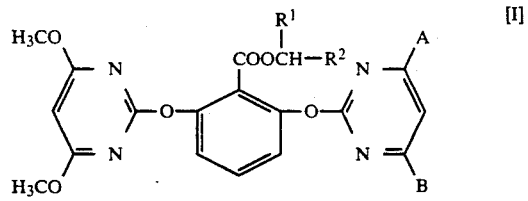

{wherein $R^1$ is a hydrogen atom or an alkyl group, $R^2$ is a group having the formula $R^3O$ (wherein $R^3$ is an alkoxyalkyl group, an aralkyl group, an alkylcarbonyl group, a phenylcarbonyl group, a substituted phenylcarbonyl group or an alkoxycarbonyl group), a group having the formula

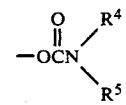

wherein $R^4$ and $R^5$ may be the same or different and are a hydrogen atom or an alkyl group), a group having the formula

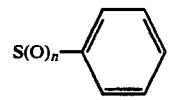

(wherein n is 0 or 1), a phthalimide group or a dioxolanylmethyl group, and A and B may be the same or different and are an alkyl group, an alkoxy group, a haloalkyl group, a haloalkoxy group, an amino group, a monoalkylamino group, a dialkylamino group, a cyano group or a halogen atom}, and a herbicidal composition containing said pyrimidine derivative as an active ingredient.

8 Claims, No Drawings

PYRIMIDIEN DERIVATIVES AND HERBICIDAL COMPOSITIONS CONTAINING THE SAME

The present invention relates to novel pyrimidine derivatives and to herbicidal compositions containing said pyrimidine derivatives as active ingredients, which can be applied to paddy fields, upland fields or non-agricultural fields.

U.S. Pat. No. 4,248,619 (Japanese Unexamined Patent Publication No. 24195/1980), U.S. Pat. No. 4,427,437 (Japanese Unexamined Patent Publication No. 55729/1979), U.S. Pat. No. 4,906,285 (Japanese Unexamined Patent Publication No. 250365/1989), and Agr. Biol. Chem., Vol. 30, No. 9, p.896 (1966) disclose that 2-phenoxypyrimidine derivatives have herbicidal activities.

Heretofore, it has been known that the bis-pyrimidinyloxybenzoic acid derivatives among pyrimidine derivatives have excellent herbicidal effect and safety. However, when they are used as herbicidal compositions, it is a general demand required for agricultural chemicals to reduce the scattering amount of an effective ingredient by improving the herbicidal effect. Also, agricultural chemicals having less influence on environments are preferable, and are required to be so improved as that they are not lost by flowing when applied to paddy fields and as that their effects remain.

Thus, the present inventors have found that compounds having the benzoic acid part esterified, exhibit excellent herbicidal effects against perennial weeds as well as annual weed, and at the same time, they have a high level of safety to crop plants, particularly to rice and wheat, and achieved the present invention based thereon.

An object of the present invention is to provide a novel pyrimidine derivative having the formula,

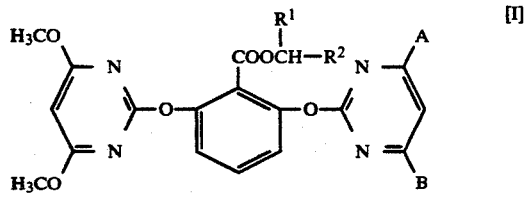

{wherein $R^1$ is a hydrogen atom or an alkyl group, preferably a $C_1$-$C_4$ alkyl group, $R^2$ is a group having the formula -$OR^3$ (wherein $R^3$ is an alkoxyalkyl group, preferably a $C_1$-$C_4$ alkoxyalkyl group, an aralkyl group, an alkylcarbonyl group, preferably a $C_1$-$C_4$ alkylcarbonyl group, a phenylcarbonyl group, a substituted phenylcarbonyl group or an alkoxycarbonyl group, preferably a $C_1$-$C_5$ alkoxycarbonyl group), a group having the formula

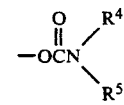

(wherein $R^4$ and $R^5$ may be the same or different and are a hydrogen atom or an alkyl group, preferably a $C_1$-$C_4$ alkyl group), a group having the formula

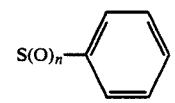

(wherein n is 0 or 1 ), a phthalimide group or a dioxeranylmethyl group, and A and B may be the same or different and are an alkyl group, preferably a $C_1$-$C_4$ alkyl group, an alkoxy group, preferably a $C_1$-$C_4$ alkoxy group, a haloalkyl group, preferably a $C_1$-$C_4$ haloalkyl group, a haloalkoxy group, preferably a $C_1$-$C_4$ haloalkoxy group, an amino group, a monoalkylamino group, a dialkylamino group, a pyrrolidin-1-yl group, a cyano group or a halogen atom}; and a herbicidal composition containing said pyrimidine derivative as an active ingredient.

Typical examples of the compound expressed by the general formula [I] of the present invention are listed in the following Table 1. Compound Nos. are used in the same meanings hereinafter.

TABLE 1

[I]

| Compound No. | $R^1$ | $R^2$ | A | B | Melting point (°C.) or Refractive Index ($n_D^{20}$) |
|---|---|---|---|---|---|
| 1 | H | S—⌬ | $OCH_3$ | $OCH_3$ | 89-93 |
| 2 | H | SO—⌬ | $OCH_3$ | $OCH_3$ | Unmeasurable |

TABLE 1-continued

[1]

Structure: 2,6-bis[(4,6-dimethoxypyrimidin-2-yl)oxy]benzoate with substituent -COOCH(R¹)-R² on central benzene ring; pyrimidine substituents A and B.

| Compound No. | R¹ | R² | A | B | Melting point (°C.) or Refractive Index ($n_D^{20}$) |
|---|---|---|---|---|---|
| 3 | H | OC(=O)—C₄H₉-t | OCH₃ | OCH₃ | 94–95 |
| 4 | H | phthalimido (N-linked) | OCH₃ | OCH₃ | 192–195 |
| 5 | CH₃ | OCOOC₂H₅ | OCH₃ | OCH₃ | 97–100 |
| 6 | H | CH₂CH(O-)(O-) (1,3-dioxolane) | OCH₃ | OCH₃ | Unmeasurable |
| 7 | H | OCH₂—C₆H₅ | OCH₃ | OCH₃ | 1.5685 |
| 8 | H | OC(=O)CH₃ | OCH₃ | OCH₃ | 97–99 |
| 9 | CH₃ | OC(=O)CH₃ | OCH₃ | OCH₃ | 110–111 |
| 10 | H | OC(=O)C₃H₇-i | OCH₃ | OCH₃ | 82–83 |
| 11 | CH₃ | OC(=O)C₃H₇-i | OCH₃ | OCH₃ | Unmeasurable |
| 12 | H | OC(=O)—C₆H₅ | OCH₃ | OCH₃ | 109–110 |
| 13 | CH₃ | OC(=O)—C₆H₅ | OCH₃ | OCH₃ | Unmeasurable |
| 14 | CH₃ | OC(=O)C₄H₉-t | OCH₃ | OCH₃ | 118–121 |
| 15 | H | OCOOC₂H₅ | OCH₃ | OCH₃ | |
| 16 | H | OC₂H₄OCH₃ | OCH₃ | OCH₃ | 100–101.5 |

TABLE 1-continued

[I]
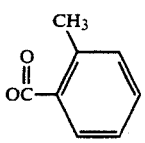

| Compound No. | R¹ | R² | A | B | Melting point (°C.) or Refractive Index ($n_D^{20}$) |
|---|---|---|---|---|---|
| 17 | i-$C_3H_7$ | $\underset{OCCH_3}{\overset{O}{\parallel}}$ | $OCH_3$ | $OCH_3$ | 1.5415 |
| 18 | $C_2H_5$ | $\underset{OCC_2H_5}{\overset{O}{\parallel}}$ | $OCH_3$ | $OCH_3$ | 1.5341 |
| 19 | H | 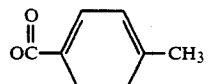 | $OCH_3$ | $OCH_3$ | 116–118 |
| 20 | H | 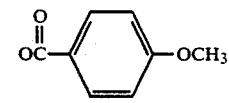 | $OCH_3$ | $OCH_3$ | 118–120.5 |
| 21 | H | 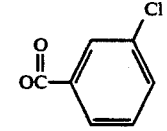 | $OCH_3$ | $OCH_3$ | 117–120 |
| 22 | H | 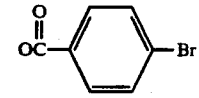 | $OCH_3$ | $OCH_3$ | 106–109 |
| 23 | H | 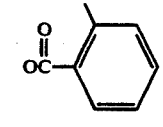 | $OCH_3$ | $OCH_3$ | |
| 24 | H | 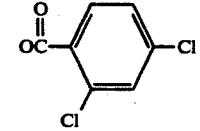 | $OCH_3$ | $OCH_3$ | |
| 25 | H | 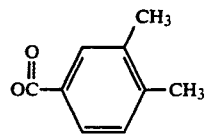 | $OCH_3$ | $OCH_3$ | |
| 26 | H | (3,4-dimethylphenyl carbonyloxy) | $OCH_3$ | $OCH_3$ | |
| 27 | H | $\underset{OCC_4H_9\text{-}t}{\overset{O}{\parallel}}$ | $OC_2H_5$ | Cl | 1.5420 |
| 28 | H | $\underset{OCC_4H_9\text{-}t}{\overset{O}{\parallel}}$ | $OCH_3$ | Cl | 83–85 |

TABLE 1-continued

[I]

$$\text{structure shown: 2,6-bis[(4,6-dimethoxypyrimidin-2-yl)oxy]... with substituents } R^1, R^2, A, B$$

| Compound No. | $R^1$ | $R^2$ | A | B | Melting point (°C.) or Refractive Index ($n_D^{20}$) |
|---|---|---|---|---|---|
| 29 | H | $OCC_4H_9\text{-}t$ (O=) | $OCH_3$ | CN | Unmeasurable |
| 30 | H | $OCC_4H_9\text{-}t$ (O=) | Cl | $N(CH_3)_2$ | 106–109 |
| 31 | H | $OCC_4H_9\text{-}t$ (O=) | $CF_3$ | $OCH_3$ | Unmeasurable |
| 32 | $CH_3$ | $OCOC_2H_5$ (O=) | $OC_3H_7\text{-}i$ | $OCH_3$ | Unmeasurable |
| 33 | H | $OCC_4H_9\text{-}t$ (O=) | $OC_4H_9\text{-}t$ | $OCH_3$ | Unmeasurable |
| 34 | $CH_3$ | $OCOC_2H_5$ (O=) | $N(CH_3)_3$ | $OCH_3$ | Unmeasurable |
| 35 | H | $OCC_2H_5$ (O=) | $OCH_3$ | $OCH_3$ | 107–108 |
| 36 | H | $OCC_3H_7\text{-}n$ (O=) | $OCH_3$ | $OCH_3$ | 78–80 |
| 37 | H | $OCC_4H_9\text{-}n$ (O=) | $OCH_3$ | $OCH_3$ | 91–96 |
| 38 | $CH_3$ | $OCC_4H_9\text{-}n$ (O=) | $OCH_3$ | $OCH_3$ | 62–65 |
| 39 | H | $OCC_4H_9\text{-}i$ (O=) | $OCH_3$ | $OCH_3$ | 77–78 |
| 40 | $CH_3$ | $OCC_4H_9\text{-}i$ (O=) | $OCH_3$ | $OCH_3$ | 1.5289 |
| 41 | H | $OCC_4H_9\text{-}s$ (O=) | $OCH_3$ | $OCH_3$ | 67–69 |
| 42 | $CH_3$ | $OCC_4H_9\text{-}s$ (O=) | $OCH_3$ | $OCH_3$ | 1.5329 |
| 43 | $CH_3$ | $OCOC_4H_9\text{-}t$ (O=) | $OCH_3$ | $OCH_3$ | 74–76 |
| 44 | $CH_3$ | $OCC_2H_5$ (O=) | $OCH_3$ | $OCH_3$ | 88–94 |
| 45 | $CH_3$ | $OCC_3H_7\text{-}n$ (O=) | $OCH_3$ | $OCH_3$ | 96–97.5 |

TABLE 1-continued

[Structure I: dimethoxy-pyrimidine-O-phenyl(COOCH(R¹)-R²)-O-pyrimidine(A,B)]

| Compound No. | $R^1$ | $R^2$ | A | B | Melting point (°C.) or Refractive Index ($n_D^{20}$) |
|---|---|---|---|---|---|
| 46 | $CH_3$ | $OCC_5H_{11}\text{-}n$ (O=) | $OCH_3$ | $OCH_3$ | 1.5350 |
| 47 | H | $OCC_4H_9\text{-}t$ (O=) | $-N\smalltriangleup$ (pyrrolidinyl) | $OCH_3$ | Unmeasurable |

The compound of the present invention can be prepared, for example, by the following process:

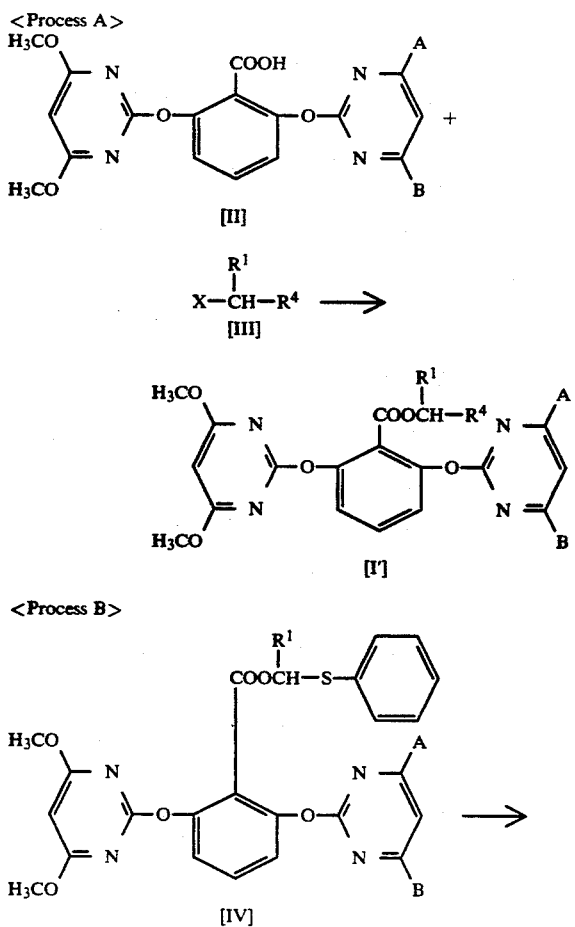

<Process A>
[II] + [III] X—CH(R¹)—R⁴ → [I']

<Process B>
[IV] →

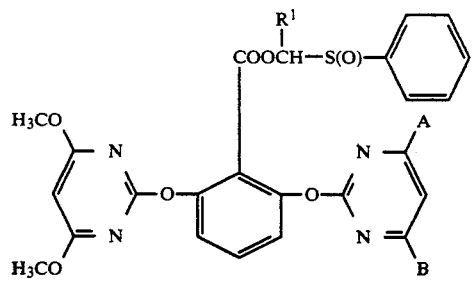

(wherein $R^1$ is as defined above, $R^4$ is a group having the formula $R^3O$ (wherein $R^3$ is as defined above), a phenylthio group, a phthalimide group or a dioxeranylmethyl group, A and B are as defined above, and X is a halogen atom).

<Process A>

The compound of the formula [I'] of the present invention can be prepared by reacting the compound of the formula [II] with the compound of the formula [III] in the presence of more than equivalent amount of a base in a solvent at a temperature in the range of from room temperature to the boiling point of the solvent for from 0.5 to 48 hours. As the base, there may be employed an alkali metal such as metallic sodium, metallic potassium or the like; an alkali metal hydride and an alkaline earth metal hydride such as sodium hydride, potassium hydride, calcium hydride or the like; an alkali metal carbonate such as sodium carbonate, potassium carbonate or the like; and an organic amine such as triethyl amine, pyridine or the like.

As the solvent, there may be employed, a hydrocarbon solvent such as benzene, toluene, xylyne or the like; a halogenated hydrocarbon solvent such as methylene chloride, chloroform or the like; an alcohol solvent such as methanol, ethanol, 2-propanol or the like; an ether solvent such as diisopropyl ether, tetrahydrofuran, dioxane or the like; a ketone solvent such as acetone, methyl ethyl ketone or the like; an ester solvent such as methyl acetate, ethyl acetate or the like; an aprotic polar solvent such as dimethylformamide, dimethylacetamide, dimethylsulfoxide or the like; and other solvents such as acetonitrile; or combinations of these solvents.

Now, the compound of the formula [II] can be prepared in accordance with the method as disclosed in Japanese Unexamined Patent Publication No. 250365/1989.

<Process B>

The compound of the formula [I] wherein $R^2$ is

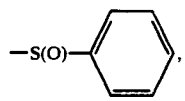

can be prepared by oxidizing the compound of the formula [IV] with an oxidizing agent in a solvent.

Now, the present invention will be described in further detail with reference to Examples. However, it should be understood that the present invention is by no means restricted to such specific Examples.

EXAMPLE 1

Preparation of 1-ethoxycarbonyloxyethyl 2,6-bis[(4,6-dimethoxypyrimidin -2-yl)oxy]benzoate (Compound No. 5)

1.7 g (4.0 mmol) of 2,6-bis[(4,6-dimethoxypyrimidin-2-yl) oxy]benzoic acid and 0.2 g of 60% sodium hydride were dissolved in N,N-dimethylformamide. After the generation of hydrogen ceased, 0.68 g (4.4 mmol) of 1-chloroethylethylcarbonate was added to the solution and the resultant mixture was reacted at 100° C. for 1 hour. After completing the reaction, the reaction mixture was added to ice water and was extracted with ethyl acetate. The ethyl acetate layer was dried with anhydrous sodium sulfate, and the ethyl acetate was distilled off. The residue was purified by silica gel column chromatography, and ethanol/hexane were added thereto to precipitate a solid, which was then filtered out to obtain 1.4 g of a white crystal having a melting point of from 97° to 100° C.

EXAMPLE 2

Preparation of 2,2-dimethylpropanoyloxymethyl 2-(4-chloro -6-methoxypyrimidin-2-yl)oxy-6-(4,6-dimethoxypyrimidin -2-yl)oxybenzoate (compound No. 28)

0.9 g of (2.1 mmol) of 2-(4-chloro-6-methoxypyrimidin -2-yl)oxy-6-(4,6-dimethoxypyrimidin-2-yl) oxybenzoic acid, 0.1 g of 60% sodium hydride and 0.39 g (2.5 mmol) of chloromethylpivalate were reacted in N,N-dimethylformamide, treated and purified in the same manner as in Example 1. To the residue thus obtained, were added ethanol/hexane to precipitate a solid, which was filtered out to obtain 0.6 g of a white crystal having a melting point of from 83° to 85° C.

EXAMPLE 3

Preparation of phenylthiomethyl 2,6-bis[(4,6-dimethoxypyrimidin -2-yl)oxy]benzoate (compound No. 1)

1.7 g (4.0 mmol) of 2,6-bis[(4,6-dimethoxypyrimidin-2-yl) oxy]benzoic acid, 0.2 g of 60% sodium hydride and 0.72 g (4.4 mmol) of chloromethylsulfide were reacted in N,N-dimethylformamide, treated and purified in the same manner as in Example 1 to obtain 1.4 g of a white crystal having a melting point of from 89° to 93° C.

EXAMPLE 4

Preparation of phenylsulphenylmethyl 2,6-bis[(4,6-dimethoxypyrimidin -2-yl)oxy]benzoate (compound No. 2)

0.7 g (1.3 mmol) of phenylthiomethyl 2,6-bis[(4,6-dimethoxypyrimidin -2-yl)oxy]benzoate was dissolved in chloroform, and thereafter a chloroform solution having 0.25 g of m-chloroperpenzoic acid dissolved was added dropwise to the above chloroform solution at a temperature of from 5° to 10° C. in an ice bath. After reacting the resultant mixture at the same temperature for 1 hour, an aqueous solution of sodium sulfite was added thereto and the mixture was separated by a separatory funnel. Thereafter, the organic layer was washed with an aqueous solution of sodium hydrogencarbonate, dried and concentrated to obtain a light brown viscous liquid. The product thus obtained was purified by column chromatography to obtain 0.6 g of a milky white resinous material.

The herbicidal composition of the present invention comprises a herbicidally effective amount of the compound of the present invention and an agricultural adjuvant.

The herbicide of the present invention may be used as it is or may be formulated in various formulations such as a wettable powder, a granule, an emulsifiable concentrate or a dust by blending it in an amount of from 0.5 to 95 parts by weight, preferably from 1 to 80 parts by weight, with a carrier, a surfactant, a dispersing agent or an adjuvant which is commonly employed for the formulation of agricultural chemicals, in an amount to make up the total of 100 parts by weight.

As the carrier to be used for the formulation, there may be mentioned a solid carrier such as jeeklite, talc, bentonite, clay, kaolin, diatomaceous earth, white carbon, vermiculite, slaked lime, silica sand, ammonium sulfate or urea, or a liquid carrier such as isopropyl alcohol, xylene, cycloheaane or methyl naphthalene. As the surfactant and dispersing agent, there may be mentioned, for example, an alcohol-sulfuric acid ester, an alkyl aryl sulfonate, lignin sulfonate, a polyoxyethylene glycol ether, a polyoxyethylene alkyl aryl ether or a polyoxyethylene sorbitol mono-alkylate. As the adjuvant, for example, carboxymethyl cellulose, polyethylene glycol or gum arabic may be mentioned.

The proportion of the compound of the present invention in the formulation may vary depending upon the type of the formulation, the application method, the application site, timing, etc. Therefore, it can not generally be defined. However, it is usually from 5 to 90% by weight in a wettable powder, from 5 to 80% by weight in an emulsifiable concentrate, from 1 to 60% by weight in a flowable, from 0.5 to 20% by weight in a granule, from 5 to 40% by weight in a liquid formulation, from 0.5 to 10% by weight in a dust and from 5 to 90% by weight in a dry flowable.

A liquid formulation can be prepared either by using the active ingredient in the form of a salt, or by adding a basic substance to the active ingredient in the form of an acid at the time of formulation. In practical use, such a herbicide may be diluted to a suitable concentration before application, or may directly be applied.

The herbicide of the present invention is capable of controlling various weeds in an agricultural field such as an upland field or an orchard, or in a forest, a lawn or other non-agricultural field by soil treatment before or after the emergence of weeds or by foliage treatment. Further, the herbicide is capable of controlling various weeds in a paddy field by irrigated soil treatment before or after the emergence of weeds or by foliage treatment.

For soil treatment, the herbicide of the present invention is applied in a dose of from 0.1 g to 1 kg, preferably from 0.5 to 500 g, more preferably from 1 to 100 g, of the active ingredient per 10 areas. For foliage treatment, it is diluted to a concentration of from 1 to 10,000 ppm for application. Most preferably, it is applied in a dose of from 1 to 10 g of the active ingredient per 10 areas for a paddy field, in a dose of from 5 to 50 g per 10 areas for an orchard or a lawn, and in a dose of from 10 to 100 g for a forest or a non-agricultural field.

If desired, the compound of the present invention may be used in combination with insecticides, sterilizers, other herbicides, plant growth controlling agents, fertilizers or the like.

Now, typical Formulation Examples for the herbicidal composition of the present invention will be given. However, it should by understood that the present invention is by no means restricted to these specific Formulation Examples. In these Examples, "part" means "part by weight".

FORMULATION EXAMPLE 1

(wettable powder)

10 Parts of Compound No. 1, 0.5 part of Emulgen 810 (trademark, Kao Corporation), 0.5 part of Demol N (trademark, Kao Corporation), 20 parts of Kunilite 201 (trade mark, Kunimine Kogyo K.K.) and 69 parts of Jeeklite CA (trademark, Jeeklite Company Ltd.) were uniformly mixed and pulverized to obtain a wettable powder.

FORMULATION EXAMPLE 2

(wettable powder)

10 Parts of Compound No. 2, 0.5 part of Emulgen 810, 0.5 part of Demol N, 20 parts of Kunilite 201, 5 parts of Carplex 80 and 64 parts of Jeeklite CA were uniformly mixed and pulverized to obtain a wettable powder.

FORMULATION EXAMPLE 3

(emulsifiable concentrate)

30 Parts of Compound No. 5, 60 parts of equivalent amount mixture of xylene and isophorone, and 10 parts of surface active agent Sorpol 800A (trademark, Toho Kagaku Kogyo K.K.) were uniformly mixed and stirred to obtain an emulsifiable concentrate.

FORMULATION EXAMPLE 4

(granule)

10 Parts of Compound No. 7, 80 parts of a bulking agent comprising a 1:3 mixture of talc and bentonite, 5 parts of white carbon, 5 parts of surface active agent Sorpol 800A and 10 parts of water were fully kneaded to obtain a paste-like material. The paste-like material was then extruded through a sieve aperture of 0.7 mm in diameter, and the extruded product was dried and cut into pieces of 0.5 to 1 mm in length to obtain granules.

The compounds and the herbicidal compositions of the present invention are capable of effectively controlling annual weeds such as barnyardgrass (*Echinochloa crusgalli*), crabgrass (*Diqitaria sanquinalis*), goosegrass (*Eleusine indica*), green foxtail (*Setaria viridis*), water foxtail (*Alopecurus aequalis*), annual bluegrass (*Poa annua*), black grass (*Alopecurus myosuroides*), wild oat (*Avena fatua*), italian ryegrass (*Lolium multiflorum*), smartweed (*Polyqonum lapathifolium*), slender amaranth (*Amaranthus viridis*), lambsquarters (*Chenopodium album*), velvetleaf (*Abutilon theophrasti*), prickly sida (*Siaa spinosa*), sicklepod (*Cassia tora*), chickweed (*Stellaria media*), morningglory (*Ipomoea spp*), common cocklebur (*Xanthium strumarium*), rice flatsedge (*Cyperus iria*), broadleaf signalgrass (*Brachiaria platyphylla*), itchgrass (*Rottoboelia exaltata*), downy brome (*Bromus tectorum*), wild buckwheat (*Polyqonum convolvulus*), wild mustard (*Brassica arvensis*) and devils beggarticks (*Bidens frondasa*), and perennial weeds such as purple nutsedge (*Cyperus rotundus*), johnsongrass (*Sorghum halepense*), bermudagrass (*Cynodon dactylon*) and quackgrass (*Aqropyron repens*) grown in upland fields including agricultural fields, orchards and non-agricultural fields.

Further, they are capable of effectively controlling annual weeds such as barnyardgrass (*Echinochloa crusqalli*), small flower flatsedge (*Cyperus difformis*), monochoria (*Monochoria vaginalis*), and perennial weeds such as bulrush (*Scirpus hotarui*) *Alisma canaliculatum*, *Cyperus serotinus*, *Saqittaria pyqmaea* and *Eleocharis kuroquwai*, grown in paddy fields.

On the other hand, the herbicides of the present invention are highly safe to crop plants, particularly rice, wheat, barley, corn, or the like.

These effects of the compounds and the herbicides of the present invention are equivalent to those of the conventional bispyrimidinyloxybenzoic acid derivatives and the herbicides containing the same as active ingredients, but are more superior in the application to the water surface of a paddy field as compared with those of the conventional ones.

The compound of the present invention hardly moves into soil as compared with the conventional bispyrimidyloxybenzoic acid type compound, and therefore the present compound has less influence on environmental polution than the conventional compound. Now, the herbicidal activities of the compounds and the herbicides of the present invention will be described with reference to Test Examples.

TEST EXAMPLE 1

(herbicidal effect test by upland field foliage treatment)

In a plastic pot filled with upland soil (surface area 120 cm$^2$), seeds of barnyardgrass (Ec), pale smartweed (Po), slender amaranth (Am), and lambsquarters (Ch) are sown to a depth of 0.5 to 1 cm, and were cultured in a green house for 2 weeks. A predetermined amount of a wettable powder prepared in accordance with Formulation Example 1 was diluted with water, and applied by a small-sized sprayer onto the foliage in an amount of 100 1/10 ares so that the dose of the active ingredient was 400 g/10 ares. The plants were cultured in the green house, and the evaluation was conducted on the 14th day after the treatment in accordance with the standard as identified in the following Table 2-1. The test results are shown in the following Table 3.

TABLE 2-1

| Index No. | Herbicidal effect |
|---|---|
| 0 | Herbicidal effect: more than 0% and less than 10% |
| 1 | Herbicidal effect: at least 10% and less than 30% |
| 2 | Herbicidal effect: at least 30% and less than 50% |
| 3 | Herbicidal effect: at least 50% and less than 70% |

TABLE 2-1-continued

| Index No. | Herbicidal effect |
|---|---|
| 4 | Herbicidal effect: at least 70% and less than 90% |
| 5 | Herbicidal effect: at least 90% |

TABLE 2-2

| Index No. | Phytotoxicity |
|---|---|
| 0 | Phytotoxicity: more than 0% and less than 10% |
| 1 | Phytotoxicity: at least 10% and less than 30% |
| 2 | Phytotoxicity: at least 30% and less than 50% |
| 3 | Phytotoxicity: at least 50% and less than 70% |
| 4 | Phytotoxicity: at least 70% and less than 90% |
| 5 | Phytotoxicity: at least 90% to completely withered |

TABLE 3

| Compound No. | Herbicidal Effect | | | |
|---|---|---|---|---|
| | Ec | Po | Am | Ch |
| 2 | 3 | 5 | 5 | 5 |
| 3 | 5 | 5 | 5 | 5 |
| 5 | 5 | 5 | 5 | 5 |
| 6 | 4 | 5 | 5 | 4 |
| 7 | 5 | 5 | 5 | 5 |
| 8 | 5 | 5 | 5 | 5 |
| 9 | 5 | 5 | 5 | 5 |
| 10 | 5 | 5 | 5 | 5 |
| 11 | 5 | 5 | 5 | 5 |
| 12 | 5 | 5 | 5 | 4 |
| 13 | 5 | 5 | 5 | 5 |
| 14 | 5 | 5 | 5 | 4 |
| 16 | 5 | 5 | 5 | 5 |
| 17 | 5 | 5 | 5 | 5 |
| 18 | 5 | 5 | 5 | 5 |
| 20 | 5 | 5 | 5 | 4 |
| 21 | 5 | 5 | 5 | 5 |
| 22 | 5 | 5 | 5 | 5 |
| 27 | 5 | 5 | 5 | 5 |
| 28 | 5 | 5 | 5 | 5 |
| 29 | 5 | 5 | 5 | 5 |
| 30 | 4 | 5 | 5 | 5 |
| 31 | 5 | 5 | 5 | 5 |
| 32 | 5 | 5 | 5 | 5 |
| 33 | 4 | 3 | 5 | 4 |
| 34 | 5 | 5 | 5 | 5 |
| 35 | 5 | 5 | 5 | 5 |
| 36 | 5 | 5 | 5 | 5 |
| 37 | 5 | 5 | 5 | 5 |
| 38 | 5 | 5 | 5 | 5 |
| 39 | 5 | 5 | 5 | 5 |
| 40 | 5 | 5 | 5 | 5 |
| 41 | 5 | 5 | 5 | 5 |
| 42 | 5 | 5 | 5 | 5 |
| 43 | 5 | 5 | 5 | 5 |
| 44 | 5 | 5 | 5 | 5 |
| 45 | 5 | 5 | 5 | 4 |
| 46 | 5 | 5 | 5 | 5 |

TEST EXAMPLE 2

(herbicidal effect test by upland field soil treatment)

In a plastic pot filled with upland field soil (surface area: 120 cm$^2$), crabgrass (Di), pale smartweed (Po), slender amaranth (Am), and lambsquarters (Ch) were sown to a depth of 0.5 to 1 cm and covered with soil. Next day, a predetermined amount of a wettable powder prepared in accordance with Formulation Example 1 was diluted with water and applied uniformly to the soil surface by a small-sized sprayer in an amount of 100 l/10 ares so that the dose of the active ingredient was 400 g/10 ares. The pot was then cultured in a green house, and the evaluation was conducted on the 21st day after the treatment in accordance with the standard as identified in the above Table 2-1. the test results are shown in the following Table 4.

TABLE 4

| Compound No. | Herbicidal Effect | | | |
|---|---|---|---|---|
| | Di | Po | Am | Ch |
| 3 | 5 | 5 | 5 | 5 |
| 5 | 5 | 5 | 5 | 5 |
| 7 | 5 | 5 | 5 | 5 |
| 8 | 5 | 5 | 5 | 5 |
| 13 | 5 | 5 | 5 | 5 |
| 14 | 5 | 5 | 5 | 5 |
| 16 | 5 | 5 | 5 | 5 |
| 17 | 5 | 5 | 5 | 5 |
| 18 | 5 | 5 | 5 | 5 |
| 19 | 5 | 5 | 5 | 5 |
| 20 | 5 | 5 | 5 | 5 |
| 21 | 5 | 5 | 5 | 5 |
| 22 | 5 | 5 | 5 | 5 |
| 27 | 5 | 5 | 5 | 5 |
| 28 | 5 | 5 | 5 | 5 |
| 29 | 4 | 5 | 5 | 5 |
| 30 | 5 | 5 | 5 | 5 |
| 31 | 5 | 5 | 5 | 5 |
| 32 | 4 | 4 | 5 | 5 |
| 34 | 3 | 4 | 5 | 5 |
| 35 | 5 | 5 | 5 | 5 |
| 36 | 5 | 5 | 5 | 5 |
| 37 | 5 | 5 | 5 | 5 |
| 38 | 5 | 5 | 5 | 5 |
| 39 | 5 | 5 | 5 | 5 |
| 40 | 5 | 5 | 5 | 5 |
| 41 | 5 | 5 | 5 | 5 |
| 42 | 5 | 5 | 5 | 5 |
| 43 | 5 | 5 | 5 | 5 |
| 44 | 5 | 5 | 5 | 5 |
| 45 | 5 | 5 | 5 | 5 |
| 46 | 5 | 5 | 5 | 5 |

TEST EXAMPLE 3

(crop selectivity test by upland field foliage treatment)

In a plastic pot (surface area: 600 cm$^2$) filled with upland field soil, rice (Or), wheat (Tr), corn (Ze), barnyardgrass (Ec), johnsongrass (So), black grass (Al), pale smartweed (Po), slender amaranth (Am) and common cocklebur (Xa) were sown to a depth of 0.5 to 1 cm and were cultured in a green house for 2 weeks. A predetermined amount (active ingredient, g/10 ares) of a wettable powder prepared in accordance with Formulation Example 1 was diluted with water, and applied onto the foliage by a small-sized sprayer in an amount of 100 l/10 ares. The plants were then cultured in the green house, and the evaluations of the herbicidal effect and phytotoxicity were conducted on the 14th day after the treatment in accordance with the standard as identified in the above Tables 2-1 and 2-2. The results are shown in the following Table 5.

TABLE 5

| Compound No. | Dose (active ingredient, g/10 ares) | Phytotoxicity | | | Herbicidal Effect | | | | | |
|---|---|---|---|---|---|---|---|---|---|---|
| | | Or | Tr | Ze | Ec | So | Al | Po | Am | Xa |
| 3 | 1.6 | 0 | 1 | 1 | 5 | 5 | 5 | 5 | 5 | 5 |
| 5 | 1.6 | 1 | 2 | 1 | 5 | 5 | 5 | 5 | 5 | 5 |
| 7 | 1.6 | 0 | 1 | 1 | 5 | 5 | 5 | 5 | 5 | 4 |
| 8 | 1.6 | 0 | 0 | 0 | 5 | 4 | 5 | 5 | 5 | 5 |
| 9 | 1.6 | 0 | 1 | — | 5 | 5 | 5 | 5 | 5 | 4 |
| 10 | 1.6 | 1 | 2 | 1 | 5 | 5 | 5 | 5 | 5 | 5 |
| 11 | 1.6 | 0 | 2 | 1 | 5 | 5 | 5 | 5 | 5 | 5 |
| 12 | 1.6 | 0 | 1 | 1 | 5 | 4 | 5 | 5 | 5 | 4 |
| 13 | 6.3 | 0 | 1 | 1 | 5 | 5 | 5 | 5 | 4 | 5 |
| 16 | 6.3 | 0 | 1 | 2 | 5 | 5 | 5 | 5 | 5 | 5 |
| 17 | 6.3 | 0 | — | 1 | 5 | 5 | 5 | 5 | 5 | 5 |
| 18 | 6.3 | 0 | — | 1 | 5 | 5 | 5 | 5 | 5 | 5 |

TABLE 5-continued

| Compound No. | Dose (active ingredient, g/10 ares) | Phytotoxicity | | | Herbicidal Effect | | | | | |
|---|---|---|---|---|---|---|---|---|---|---|
| | | Or | Tr | Ze | Ec | So | Al | Po | Am | Xa |
| 22 | 6.3 | 0 | 0 | 1 | 4 | 5 | 5 | 5 | 4 | 5 |
| 35 | 1.6 | 0 | 1 | 2 | 5 | 4 | 5 | 5 | 5 | 4 |
| 36 | 1.6 | 0 | 2 | — | 5 | 5 | 5 | 5 | 5 | 5 |
| 38 | 1.6 | 0 | 2 | 2 | 5 | 5 | 5 | 5 | 5 | 5 |
| 39 | 1.6 | 0 | 2 | 2 | 5 | 4 | 5 | 5 | 5 | 4 |
| 40 | 1.6 | 0 | 2 | 2 | 5 | 4 | 5 | 4 | 5 | 5 |
| 41 | 1.6 | 0 | 2 | 1 | 5 | 5 | 5 | 5 | 5 | 5 |
| 42 | 1.6 | 0 | 1 | 1 | 5 | 5 | 5 | 4 | 5 | 4 |
| 43 | 1.6 | 0 | 1 | 1 | 5 | 5 | 5 | 4 | 4 | 4 |
| 44 | 1.6 | 0 | 1 | 2 | 5 | 5 | 4 | 5 | 5 | 4 |
| 45 | 1.6 | 0 | 1 | 1 | 5 | 5 | 5 | 5 | 5 | 4 |
| 46 | 1.6 | 0 | 2 | 2 | 5 | 5 | 4 | 5 | 4 | 4 |

TEST EXAMPLE 4

(crop selectivity test by paddy field soil treatment)

In a plastic pot (surface area: 1/10,000 are) filled with paddy field soil, barnyardgrass (Ec), monochoria (Mo) and bulrush (Sc) were sown to a depth of 0.5 cm after irrigating, puddling and leveling. In the pot, two pieces of paddy rice (Or) of 2.5 leaf stage were transplanted to a transplanting depth of 2 cm, and flooded to a water depth of 3 cm. Next day, a predetermined amount (active ingredient, g/10 ares) of a wettable powder prepared in accordance with Formulation Example 1 diluted with water, and applied dropwise to the water surface. The plants were then cultured in a green house, and the evaluations of the herbicidal effect and phytotoxicity were conducted on the 28th day after the treatment in accordance with the standards as identified in Tables 2-1 and 2-2. The results are shown in the following Table 6.

The following compound was used as a comparative herbicide.

Comparative Compound
2,6-bis[(4,6-dimethoxypyrimidin-2-yl)oxy]benzoic acid disclosed in Japanese Unexamined Patent Publication No. 250365/1989.)

TABLE 6

| Compound No. | Dose (active ingredient, g/10 ares) | Herbicidal Effect | | | Phytotoxicity |
|---|---|---|---|---|---|
| | | Ec | Mo | Sc | Or |
| 3 | 1.6 | 5 | 5 | 5 | 0 |
| 5 | 1.6 | 5 | 5 | 4 | 0 |
| 9 | 1.6 | 4 | 5 | 4 | 0 |
| 10 | 1.6 | 5 | 5 | 4 | 1 |
| 11 | 1.6 | 5 | 5 | 3 | 0 |
| 27 | 1.6 | 5 | 4 | 4 | 0 |
| 28 | 1.6 | 5 | 5 | 5 | 1 |
| 37 | 1.6 | 5 | 5 | 4 | 0 |
| * | 1.6 | 1 | 4 | 2 | 0 |

*: Comparative Herbicide

We claim:
1. A pyrimidine derivative having the formula,

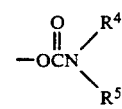

wherein $R^1$ is a hydrogen atom or a $C_1$-$C_4$ alkyl group, $R^2$ is a group having the formula —$OR^3$ wherein $R^3$ is a $C_1$-$C_4$ alkoxy $C_1$-$C_4$ alkyl group, a phenyl group, a $C_1$-$C_6$ alkylcarbonyl group, a phenylcarbonyl group, a $C_1$-$C_4$ alkyl-, $C_1$-$C_4$ alkoxy- or halogen-substituted phenylcarbonyl group or a $C_1$-$C_5$ alkoxycarbonyl group, a group having the formula

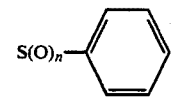

wherein $R^4$ and $R^5$ may be the same or different and are a hydrogen atom or a $C_1$-$C_4$ alkyl group, a group having the formula $$S(O)_n\text{—phenyl}$$

wherein n is 0 or 1, a phthalimide group or a dioxoranylmethyl group, and A and B may be the same or different and are a $C_1$-$C_4$ alkyl group, a $C_1$-$C_4$ alkoxy group, a halo$C_1$-$C_4$alkyl group, a halo$C_1$-$C_4$alkoxy group, an amino group, a mono$C_1$-$C_4$alkylamino group, a di$C_1$-$C_4$alkylamino group, a cyano group or a halogen atom.

2. The pyrimidine derivative according to claim 1, wherein $R^2$ is —$OR^3$ ($R^3$ is as defined above), and A and B are a $C_1$-$C_4$ alkoxy group, a halogen atom, a halo$C_1$-$C_4$alkyl group, a cyano group or a dialkylamino group.

3. The pyrimidine derivative according to claim 2, wherein A and B are a $C_1$-$C_4$ alkoxy group or a halogen atom.

4. The pyrimidine derivative according to claim 1, wherein $R^1$ is H or —$CH_3$, $R^2$ is

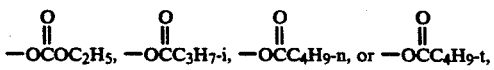

and A and B are —$OCH_3$.

5. A herbicidal composition comprising a herbicidally effective amount of a pyrimidine derivative having the formula,

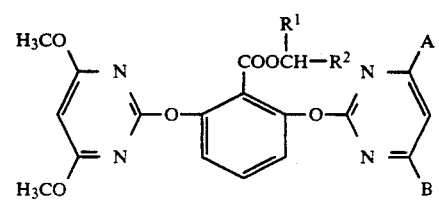

wherein $R^1$ is a hydrogen atom or a $C_1$-$C_4$ alkyl group, $R^2$ is a group having the formula —$OR^3$ wherein $R^3$ is a $C_1$-$C_4$ alkoxy $C_1$-$C_4$ alkyl group, a phenyl group, a $C_1$-$C_6$ alkylcarbonyl group, a phenylcarbonyl group, a $C_1$-$C_4$ alkyl-, $C_1$-$C_4$ alkoxy- or halogen-substituted phenylcarbonyl group or a $C_1$-$C_5$ alkoxycarbonyl group, a group having the formula

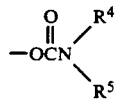

wherein $R^4$ and $R^5$ may be the same or different and are a hydrogen atom or a $C_1$-$C_4$ alkyl group, a group having the formula

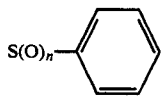

wherein n is 0 or 1, a phthalimide group or a dioxoranylmethyl group, and A and B may be the same or different and are a $C_1$-$C_4$ alkyl group, a $C_1$-$C_4$ alkoxy group, a halo$C_1$-$C_4$alkyl group, a halo$C_1$-$C_4$alkoxy group, an amino group, a mono$C_1$-$C_4$alkylamino group, a di$C_1$-$C_4$alkylamino group, a cyano group or a halogen atom, and an agricultural adjuvant.

6. The herbicidal composition according to claim 1, wherein $R^2$ is —$OR^3$ ($R^3$ is as defined above), and A and B are a $C_1$-$C_4$ alkoxy group, a halogen atom, a halo$C_1$-$C_4$alkyl group, a cyano group or a dialkylamino group.

7. The herbicidal composition according to claim 6, wherein A and B are a $C_1$-$C_4$ alkoxy group or a halogen atom.

8. The herbicidal composition according to claim 5, wherein $R^1$ is H or —$CH^3$, $R^2$ is

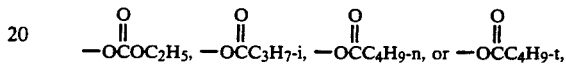

and A and B are —$OCH_3$.

* * * * *